(12) United States Patent
Wangh et al.

(10) Patent No.: US 7,465,562 B2
(45) Date of Patent: Dec. 16, 2008

(54) NUCLEIC ACID PROCESSING METHODS, KITS AND DEVICES

(75) Inventors: Lawrence J. Wangh, Auburndale, MA (US); Cristina Hartshorn, Needham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 10/557,280

(22) PCT Filed: May 18, 2004

(86) PCT No.: PCT/US2004/015611

§ 371 (c)(1), (2), (4) Date: Nov. 18, 2005

(87) PCT Pub. No.: WO2004/104181

PCT Pub. Date: Dec. 2, 2004

(65) Prior Publication Data

US 2006/0275773 A1    Dec. 7, 2006

Related U.S. Application Data

(60) Provisional application No. 60/471,895, filed on May 19, 2003.

(51) Int. Cl.
*C12P 19/34* (2006.01)
*C12Q 1/68* (2006.01)
(52) U.S. Cl. .......................... 435/91.5; 435/6; 435/91.2
(58) Field of Classification Search ........................ None
See application file for complete search history.

(56) References Cited

U.S. PATENT DOCUMENTS

| 5,407,810 | A | * | 4/1995 | Builder et al. .............. 435/69.1 |
| 5,639,599 | A | * | 6/1997 | Ryder et al. .................... 435/5 |
| 5,939,259 | A | * | 8/1999 | Harvey et al. ................... 435/6 |
| 6,440,725 | B1 | * | 8/2002 | Pourahmadi et al. ...... 435/288.5 |
| 6,762,160 | B2 | * | 7/2004 | Barbeau et al. ............. 510/161 |
| 6,777,210 | B1 | * | 8/2004 | Pasloske et al. .......... 435/91.21 |
| 2004/0259162 | A1 | * | 12/2004 | Kappel et al. ................ 435/7.1 |

FOREIGN PATENT DOCUMENTS

| WO | WO 97/05248 | 2/1997 |
| WO | WO 98/31840 | 7/1998 |

OTHER PUBLICATIONS

Vodkin et al. PCR-based detection of Arboviral RNA from mosquitoes homogenized in detergent. BioTechniques (1994) 17(1): 114-116.*
Tsai, Y.H. Cost-effective one-step PCR amplification of cystic fibrosis deltaF508 fragment in a single cell for preimplantation genetic diagnosis. Prenatal Diagnosis. (1999) 19: 1048-1051.*
Thornhill et al. A comparison of different lysis buffers to assess allele dropout from single cells for preimplantation genetic diagnosis. Prenatal Diagnosis (2001) 21: 490-497.*
Christina Hartshorn et al., "Rapid, single-tube method for quantitative preparation and analysis of RNA and DNA in samples as small as one cell", BMC Biotechnology, vol. 5, No. 2, Jan. 13, 2005, pp. 1-13.
Pierre J. Obeid et al., "Microfabricated Device for DNA and RNA Aplification by Continuous-Flow Polymerase Chain Reaction and Reverse Transcription-Polymerase Chain Reaction with Cycle Number Selection", Analytical Chemistry, vol. 75, No. 2, Jan. 15, 2003, pp. 288-295.
International Search Report (1 pg.). Oct. 2005.
Supplementary European Search Report (7 pgs.) Oct. 2007.

* cited by examiner

*Primary Examiner*—Kenneth R. Horlick
*Assistant Examiner*—Angela Bertagna
(74) *Attorney, Agent, or Firm*—Foley & Lardner LLP (57) ABSTRACT

Biological samples containing nucleic acids, RNA and DNA, are freed from bound proteins by incubation with a chaotropic agent such as a guanidium salt, and the mixture is readied for further processing by dilution of such agent to a concentration below 0.05 M without physical isolation of RNA and DNA from one another or from other components of the reaction mixture. Methods include such preparation and further processing, such as amplification and detection, which may be performed in a single container. Chaotropic agent may be supplied as a dried reagent adhered to a container. Kits may include such reagents, alone or with amplification reagents.

28 Claims, 5 Drawing Sheets

NUCLEIC ACID PROCESSING METHODS, KITS AND DEVICES

CROSS REFERENCE TO RELATED APPLICATIONS

This application is a national phase filing under 35 U.S.C. §371 of international application number PCT/US2004/015611, filed May 18, 2004, and claims the benefit of priority of U.S. provisional application number 60/471,895, filed May 19, 2003. The disclosures of the prior applications are considered part of (and are incorporated by reference in) the disclosure of this application.

TECHNICAL FIELD

This invention relates to preparation of one or more nucleic acid molecules, either DNA detection, modification, and/or manipulation with our without intervening amplification of sequences within said nucleic acid molecules.

BACKGROUND

Nucleic acid molecules, RNA and DNA, present in both cellular and non-cellular samples are often associated with proteins or other macromolecules whose binding interferes with either detection or enzymatic manipulation of the nucleic acids. For this reason most protocols designed to detect or utilize nucleic acids begin with one or more purification and/or isolation steps that are carried out prior to any subsequent manipulation, such as amplification of particular target sequences or replication of reporter sequences.

Methods used to prepare the nucleic acid must be compatible with the subsequent biochemical steps. In addition, it is preferable to perform purification in the fewest reliable steps and the smallest possible number of containers in order to reduce losses. Quantitative accuracy and convenience of use are important features of assays, which may be carried out on large numbers of small samples, for instance samples composed of only one cell, or a relatively small number of cells, or samples comprised of a small piece of tissue, a fraction of a cell, or a small volume of a cellular extract or homogenate, or non-cellular samples of nucleic acids. Handling and processing, particularly of small samples, should not result in the loss, degradation, or contamination of said samples or of the nucleic acids within such samples.

Traditional methods for the purification or isolation of DNA and RNA from cells and tissues and the separation of DNA molecules from RNA molecules, typically include, but are not limited to: a) disruption/denaturation of the sample in the presence of strong denaturant agents such as guanidine salts, urea, detergents, strong alkali, or a combination of the above; b) separation of nucleic acids of interest from denatured proteins and/or other nucleic acids by extraction with a non-aqueous liquid, such as phenol:chloroform (used for total RNA and DNA separation), or by absorption to a matrix, resin, beads or fibers (used for selective extraction of mRNA and for other applications), or by neutralization with alkaline buffer and centrifugation (used for plasmid DNA isolation); c) recovery of nucleic acids by precipitation with an alcohol or a monovalent cation such as sodium or ammonium, or lithium chloride, and re-suspension to an appropriately small volume or, alternatively, elution of nucleic acids in an appropriately small volume. The volume in which the purified nucleic acids are contained determines the fraction of nucleic acids that can be analyzed in one assay. Volume is of particular importance when analysis is carried out on very small samples such as single cells or very few cells. It is known in the art that certain starting samples require the use of harsher conditions to disrupt cells. Conditions can be chosen to selectively degrade or digest DNA or RNA for recovery of the other. RNA molecules are much more sensitive to degradation than DNA molecules, due to their sensitivity to alkaline conditions, to high temperature, and to the ubiquitous presence of RNases. Thus, many protocols for isolation of RNA require milder conditions and include the presence of agents designed to inhibit RNases.

Examples of known methods for genomic DNA or RNA purification, isolation, or separation include use of: cetyltrimethylammonium bromide (CTAB) and high salt concentration, (Jones, A. S. (1963), Use of Alkyltrimethylammonium Bromides for the Isolation of Ribo- and Deoxyribo-Nucleic Acids, Nature 199:280-282); low salt concentration under hyperbaric, hydrostatic pressure (U.S. Pat. No. 6,111,096); gentle salt precipitation (and optional protease digestion); irreversible binding to aluminum oxide-covered matrixes (U.S. Pat. No. 6,291,166); preparation of RNA by guanidinium thiocyanate lysis followed by centrifugation through a CsCl cushion (Chirgwin, J. M. et al. (1979), Isolation of Biologically Active Ribonucleic Acid from Sources Enriched in Ribonuclease, Biochemistry 18:5294-5299); various modifications and improvements of the acid guanidinium thiocyanate-phenol-chloroform method (Chomczynski, P. and Sacchi, N. (1987), Single-Step Method of RNA Isolation by Acid Guanidinium Thiocyanate-Phenol-Chloroform Extraction, Anal. Biochem. 162:156-159), later expanded to include DNA isolation (Chomczynski, P. (1993), A Reagent for the Single-Step Simultaneous Isolation of RNA, DNA and Proteins from Cell and Tissue Samples, Biotechniques 15:532-537); binding of total RNA or DNA to matrixes such as glass fiber filters, silica-gel membranes, magnetic beads or cellulose-based matrixes.

Specific extraction of mRNA molecules only is performed by interaction of their poly(A) tails with oligo (dT) attached to cellulose or resins containing a streptavidin complex; and selective precipitation of mRNA molecules with Poly T PNA probes and streptavidin. An intact poly(A) tail is probably not always present, particularly for very long RNA molecules such as Xist mRNA (Hong, Y. K. et al. (1999), A New Structure for the Murine Xist Gene and its Relationship to Chromosome Choice/Counting During X-Chromosome Inactivation, Proc. Natl. Acad. Sci. USA 96:6829-6834).

Fluorescence in situ hybridization (FISH) is an example of isolation and purification in situ. Procedures typically involve fixation of the sample, during which bound proteins are denatured, followed by washing steps in the presence of a detergent that removes at least some proteins. All these manipulations necessitate a considerable time-and-labor investment. Moreover, they all can lead to loss of nucleic acid molecules during the purification/extraction procedure or to poor detection of the target sequences. The latter can be a problem, since FISH probes need to recognize and visualize above background a very low number of target molecules.

Recently real-time target amplification methods, for example real-time PCR techniques, have provided a powerful tool for accurate quantification of RNA copy numbers, making possible the study of fine modulations of gene expression levels. As previously mentioned, however, RNA isolation is highly challenging, because of both the physical/chemical characteristic of this type of molecule and its sensitivity to the action of multiple RNases, present intracellularly or easily introduced by environmental contamination. Typically DNA is removed from RNA preparations by chemical, physical, or enzymatic methods. All of the above manipulations have contributed to shedding doubt on the reliability of RNA copy estimates obtained with the available protocols, particularly when analyzing very small samples. (See Klein, C. A. et al. (2002), Combined Transcriptome and Genome Analysis of Single Micrometastatic Cells, Nat. Biotechnol. 20:387-392).

Strategies have been devised to achieve mRNA capture, reverse transcription and PCR amplification in the same vessel, thereby limiting loss or damage of nucleic acids molecules during purification. Oligo (dT)-coated multi-well plates or streptavidin-coated PCR tubes to be used in conjunction with biotin-labeled oligo $(dT)_{20}$, for example, are used for capture. Nucleic acids shearing may be lower with such methods, and loss of material due to transfer to a new vessel is avoided, but the accuracy of RNA quantification still depends on the efficiency of mRNA-binding to the capturing molecules.

Preparation of total RNA, rather than mRNA, is an alternative for the single-tube (or single-vessel, if microchips are used) approach, provided that removal of the proteins bound to nucleic acids is achieved in a way that doesn't interfere with subsequent steps of reverse transcription (RT) and PCR and does not affect RNA integrity.

Cell lysis by a simple freeze-thaw cycle neither separates proteins from nucleic acids, nor inactivates cellular RNases. Lysis by boiling bacterial cells surely leads to RNA hydrolysis.

A Cells-to-cDNA II Kit from Ambion, Inc. (Austin, Tex. U.S.A.) employs a Cell Lysis 11 Buffer compatible with RT and PCR. RNA copies can be thus amplified in one tube while DNA is degraded via DNase digestion, as suggested by the manufacturer. RT and PCR are then carried out sequentially by addition of the appropriate buffers and reagents to the lysed sample. The Cell Lysis II Buffer/RT PCR Buffer ratio tolerated by the assay, however, is low so that only a fraction of the lysed sample can be used for each RT-PCR assay. This technique, therefore, is not suitable for the analysis of very small samples, comprised of few or single cells. Non-ionic detergents, such as Triton® X-100 or NP-40, are used in a number of protocols to lyse the cells plasma membrane and release cytoplasmic RNA pools. These detergents, at appropriate concentrations, are compatible with enzymatic reactions and cytoplasmic samples prepared with this method can be directly used in RT-PCR assays or other manipulation of RNA molecules aimed at their detection and/or quantification (Brady, G. and Iscove, N. N. (1993), Construction of cDNA Libraries from Single Cells, Methods Enzymol. 225:611-623; Hansis, C. et al. (2001), Analysis of Oct-4 Expression and Ploidy in Individual Human Blastomeres, Mol. Hum. Reprod. 7:155-161). Genomic DNA and nuclear RNA, such as Xist RNA, cannot, however, be prepared with these procedures.

Our laboratory developed an assay capable of measuring both genomic DNA and mRNA copies of genes of interest in single mouse embryos or blastomeres (Hartshorn, C., Rice J. E., Wangh, L. J. (2002), Developmentally-Regulated Changes of Xist RNA Levels in Single Preimplantation Mouse Embryos, as Revealed by Quantitative Real-Time PCR, Mol. Reprod. Dev. 61:425-436; Hartshorn, C., Rice, J. E., Wangh, L. J. (2003), Differential Pattern of Xist RNA Accumulation in Single Blastomeres Isolated from 8-cell Stage Mouse Embryos Following Laser Zona Drilling, Mol. Reprod. Dev. 64:41-51; Hartshorn, C., Rice, J. E., Wangh, L. J., Optimized Real-Time RT-PCR for Quantitative Measurements of DNA and RNA in Single Embryos and Blastomeres, In: Bustin S. A., ed. A-Z of Quantitative PCR, pages 675-702, International University Line, In press.). Counting genomic DNA copies in very small samples provides an ideal internal standard for nucleic acid recovery and for PCR efficiency. Moreover, there is no need to use DNase and the accompanying heat-inactivation of the enzyme, during which some RNA can be hydrolyzed (RNA degradation is enhanced by the presence of magnesium, required for DNase activity). Our attempts to adapt the Ambion Cells-to-cDNA II Kit to RT-PCR of RNA and DNA from single embryos/cells failed, probably due to the higher-than-recommended amount of Cell Lysis Buffer that had to be used in order to assay whole specimens rather than an aliquot of the specimen. While RNA was measured at the expected levels in high-expressing samples, genomic DNA, present in low copy numbers, was very often undetected.

Examples of lysis buffers aimed at the preparation of DNA templates only and compatible with PCR analysis in the same reaction vessel are known and commercially available. Generally these methods do not allow simultaneous/parallel analysis of DNA and RNA molecules from the same samples, because RNA is degraded during the extraction procedure. The Release-IT™ (CPG, Inc., Lincoln Park, N.J., U.S.A.) is a proprietary reagent that releases DNA from whole blood, cell cultures, bacterial colonies and other biological samples. Lysis is accomplished directly in the amplification tube on a thermal cycler, and PCR reagents are subsequently added to the lysate initiating amplification. Release-IT™ sequesters cell lysis products that might inhibit PCR. Unlike other methods described above, this allows RNA recovery and reverse transcription of small aliquots of the sample for RT-PCR (the whole sample can be used for PCR of genomic DNA). However, the initial heating cycle required for Release-IT™ action is believed to be detrimental to RNA, because it includes a total of 4 minutes at 97° C. and a holding step at 80° C. Moreover, the Release-IT™ reagent is not recommended for amplification of low copy number DNA without cellular enrichment.

Nucleic acids analysis in very small samples, including single cells or a portion of a single cell, presents a number of challenges. While several commercial kits offer RT-PCR sensitivity down to the single-cell level, this claim often implies harvesting a larger sample of which only a portion is used for each assay. A few kits promise efficient nucleic acids extraction from actual single cells, but collection of the individual samples themselves is frequently difficult and should be done carefully to preserve RNA content (Hartshorn, C., Rice, J. E., Wangh, L. J. (2003)). Recently, laser capture microdissection (LCM) and laser pressure catapulting (LPC) have made precise excision of single cells, or compartments of single cells, possible. Further, two techniques have already been developed for single-cell gene expression profiling that rely on polyadenylation of mRNA molecules for their direct detection in a cell lysate, without need for RNA purification (3 prime end amplification, or TPEA, and global amplification of cDNA copies of all polyadenylated mRNAs, or PolyAPCR) (reviewed by Brady, G. (2000), Expression Profiling of Single Mammalian Cells—Small is Beautiful, Yeast 17:211-217). Both techniques are limited to cytoplasmic RNA measurements and do not extend to DNA or nuclear RNA.

An aspect of this invention is a method for preparing DNA or RNA molecules, or both, for amplification and detection or for other enzymatic processing of mixtures of DNA and RNA molecules that have been freed of bound proteins, such mixtures comprising freed DNA and RNA molecules, a chaotropic agent, and degraded and denatured proteins, comprising diluting the mixture so as to reduce the concentration of chaotropic agent to less than 0.05 M, preferably less than 0.01

M, without removing or isolating the DNA and RNA molecules from each other or from the other components of the mixture.

Another aspect of this invention is preparing the foregoing mixture, prior to diluting it, by incubating a sample containing protein-bound DNA and RNA molecules with a concentrated disruption reagent containing at least 2 M chaotropic agent.

Another aspect of this invention is amplifying one or more DNA and RNA sequences in the diluted mixture without physically separating the DNA and RNA molecules from the diluted mixture.

A further aspect of this invention is performing the foregoing dilutions and amplifications in a single container and, preferably, also preparing the mixture in the container.

Yet another aspect of this invention is a device useful in freeing DNA and RNA molecules from bound proteins comprising a dry or semi-dry disruption reagent containing a chaotropic reagent that is adhered to a surface of a container or a container part, such as a cap of a tube or a surface within a multiple-chambered container.

Another aspect of this invention is kits including the foregoing device and additional reagents and materials for performing dilution and further processing of diluted mixtures, for example, amplification and sequencing reactions.

SUMMARY

This invention includes methods, devices and reagents for preparation of deoxyribonucleic acid (DNA) and ribonucleic acid (RNA) molecules for amplification and detection or other enzymatic processing without physical isolation of nucleic acids from denatured proteins or physical isolation of one type of nucleic acids (DNA or RNA) from the other. Preparative methods according to this invention can be performed in a single container, without any transfer of sample-containing material. Further processing, such as amplification and detection, can be performed in the container holding the prepared nucleic acids, also without any transfer of sample-containing material. Methods according to this invention include preparation, amplification and detection of nucleic acids in a single container, for example, a 200 µl tube suitable for use with current thermal cycling instruments. Methods according to this invention reduce or minimize shearing of nucleic acids by reducing or eliminating transferring, washing and resuspension of nucleic acids, thereby reducing the problem of mispriming in amplification reactions, particularly amplifications utilizing the polymerase chain reaction.

Nucleic acids sample sources to which methods of this invention can be applied include single cells, groups of cells (embryos, tissue samples), cell lysates, or other sources of nucleic acids, for example, cytoplasm sipped from cells. If the source is one or more cells, preparation includes cell lysis, which is not required if a lysate is the source. Samples to which methods of this invention are applied contain nucleic acids to which proteins are bound.

The first step in methods according to this invention is to free nucleic acids from bound proteins and to inactivate nucleases. If the sample is cellular, the first step also includes lysing the cell or cells. For the first step the sample is treated with a reagent conveniently referred to as a Disruption Reagent. The essential component of the Disruption Reagent is a chaotropic agent to denature or degrade all proteins, including nucleases. Suitable chaotropic agents include guanidium salts, such as guanidine isothiocyanate or guanidine hydrochloride, and potassium iodide. Our preferred agent is guanidine isothiocyanate. The first step is performed in a small volume, less than 10 µl of Disruption Reagent, preferably less than 1 µl and, for embodiments that include amplification in a single tube, more preferably 20-50 nl so as to permit serial dilutions without exceeding the capacity of a standard 200 µl tube. The first step is also performed at a high concentration of chaotropic agent, sufficient to achieve at least 2 M concentration of monovalent cation. Working at room temperature, guanidine isothiocyanate at high concentrations tends to precipitate (and clog small-bore pipets suitable for dispensing nanoliter quantities). To permit working with a preferred concentration of 4 M guanidine isothiocyanate, for example, we add one percent or more by volume of dimethylsulfoxide (DMSO), a water-miscible solvent that prevents precipitation but can be evaporated during a subsequent drying step. If the Disruption Reagent is not dried prior to use in processing the nucleic acids, the presence of dimethylsulfixide has the added benefit of enhancing the permeability of cell membranes to external chemicals, such as the chaotropic agent.

As indicated earlier, lysing is needed in the first step, if the sample is one or more cells. The Disruption Reagent may include a detergent for this purpose. We have used sarcosyl, obtained from Stratagene, La Jolla, Calif., U.S.A., as the detergent. Additional ingredients that may be included in the Disruption Reagent include a reducing agent, preferably one that evaporates during drying, such as βmercapto-ethanol, a chelating agent, and a neutral buffer, such as sodium citrate.

The Disruption Reagent may be used as a liquid, or it may be dried and reconstituted during use. We have successfully dried and then reconstituted to its original volume 20 nl of the following Disruption Reagent: 0.25% sarcosyl (detergent), 2 M guanidine isothiocyanate (chaotropic agent), 1% (vol/vol) DMSO (solvent), 100 mM βmercapto-ethanol (reducing agent) and 0.01 M sodium citrate, pH 7.0 (buffer).

The first step in methods according to this invention comprises incubating a sample with a Disruption Reagent for a time and temperature sufficient to permanently denature proteins that are present. In preferred embodiments the first step includes heating to concentrate the mixture by evaporation. This raises the concentration of chaotropic reagent significantly, thereby ensuring permanent protein denaturation. Although not preferred, the initial concentration of chaotropic reagent can be reduced, because, if heating is included, evaporation will concentrate the agent to or above the required 2 M concentration. Most preferably, heating is performed promptly after the sample and Disruption Reagent (reconstituted to original volume, if dried) are mixed. It is preferred that heating be sufficient to evaporate the mixture to a semi-dry (moist solid) or dry product. Such heating will evaporate DMSO and βmercapto-ethanol, if present. The duration and intensity of heating is adjusted experimentally so as to prevent loss of nucleic acid target sequence(s) of an assay or at least prevent loss from exceeding 25 percent. Dry and semi-dry product from the first step can be used immediately or stored pending further processing.

The second step in methods according to this invention is to dilute the liquid, dry or semi-dry product from the first step, either prior to or as part of further processing of nucleic acids in the mixture. For purposes of illustration, we will describe in detail processing of freed nucleic acids beginning with reverse transcription (RT). It is important that prior to or at least by this first enzymatic step, dilution of the mixture resulting from the first step be sufficient so that reagents, particularly including chaotropic agent, in the mixture at this point are reduced to a concentration that is so low that they do not significantly adversely affect the processing. In all cases the amount of dilution for further processing must be sufficient to lower the concentration of chaotropic agent to less than 0.05 M. For the illustrative processing of reverse transcription, we have found that dilution should reduce the concentration of our preferred chaotropic agent, guanidine isothiocyanate to below 0.05 M, preferably significantly lower, more preferably below 0.01 M. As can be seen from the Examples, we have successfully utilized dilution to 0.004 M guanidine isothiocyanate. The required degree of dilution for particular processing can readily be determined experimentally. In embodiments that are performed by hand, we prefer to utilize dilution volumes of at least 1 μl, as smaller volumes are difficult to pipet accurately. That will not be the case with chip-type embodiments, which may include precise machine control, and we prefer in such embodiments to minimize volumes to lower device and reagent costs to the extent practicable.

As indicated, dilution of the second step can be performed either as a single dilution or as a series of dilutions. For illustration, proceeding to reverse transcription can be performed in two dilutions: first adding water containing primers for reverse transcription, heating to melt double strands and then cooling to anneal RT primers; followed by a second dilution with reverse transcriptase in RT buffer. Using this procedure, we prefer that the first dilution itself be at least 50:1, more preferably higher, for example at least as high as 300:1; and that the second dilution, including revere transcriptase and RT buffer, complete the dilution. Also, as discussed in more detail below, other appropriate enzyme treatments (for example, DNase or a glycosidase such as cellulase, amylase, β-glucosidase or lysozyme) can be performed with dilution, either a single dilution or a series of dilutions. In the Examples we demonstrate enzyme activity with dilutions of 200:1 and 500:1.

Following completion of the second step, the sample is prepared and ready for further processing. Further processing may include amplification-and-detection assays. Such assays may include exponential amplification of target molecules or reporters, utilizing, for example, methods known in the art, such as the polymerase chain reaction (PCR) process (U.S. Pat. Nos. 4,683,202, 4,683,195, 4,965,188), nucleic acid sequence-based amplification (Heim, A. et al. (1998), Highly Sensitive Detection of Gene Expression of an Intronless Gene: Amplification of mRNA, but not Genomic DNA by Nucleic Acid Sequence Based Amplification (NASBA), Nucleic Acids Res. 26: 2250-2251, strand-displacement amplification (SDA), transcription-mediated amplification (TMA), rolling-circle amplification (RCA) (Daubendiek, S. L. and Kool, E. T. (1997), Generation of Catalytic RNAs by Rolling Transcription of Synthetic DNA Nanocircles, Nat. Biotechnol. 15: 273: 273-277), and ramification amplification methodology (RAM). Because PCR is the most widely used amplification technique, it is used herein for explanatory purposes. Persons skilled in the art will be able to apply the explanations to other amplifications techniques.

Selected sequences of the nucleic acids, both RNA and DNA resulting from the second step may be further processed by a PCR amplification assay. To amplify RNA, it is first converted to cDNA by reverse transcription. Following that, DNA—both genomic DNA and cDNA—can be amplified. One preferred method is to heat the mixture from the second step to melt double-stranded nucleic acid sequences and then to cool the mixture so as not to denature reverse transcriptase enzyme. Reverse transcriptase enzyme and its buffer are then added to the mixture of the second step, along with primers, if primers are not already present. In carrying out reverse transcription, we prefer not to further dilute the product more than necessary, preferably not more than 6:1 and even more preferably not more than 2:1 for the reason stated above.

At this point one may optionally eliminate RNA from the mixture. RNA molecules may interfere with certain processing of genomic DNA and cDNA. For this purpose we add RNase H to the mixture, so as to degrade RNA from RNA:cDNA hybrids. Again, we prefer to minimize the increase in volume from this addition, and we prefer to limit the increase to 5%. The mixture is incubated for a time and temperature sufficient for RNase digestion of RNA strands in the hybrids.

Next we add to the mixture a PCR amplification mixture containing all necessary reagents to amplify one or more selected target sequences by the polymerase chain reaction process, including all primers, precursors, polymerase enzyme, controls and PCR buffer. The polymerase chain reaction process may be a traditional symmetric PCR amplification, utilizing forward and reverse primers in equimolar amounts; an asymmetric PCR amplification, utilizing one primer in excess; or a LATE-PCR amplification, as disclosed in pending U.S. patent application Ser. No. 10/320,893, filed Dec. 17, 2002 and in published international patent application WO 03/054233. Asymmetric PCR and LATE-PCR both include exponential amplification followed by linear amplification. Alternative PCR-based amplification methods may also be used, for example, Serial Analysis of Gene Expression (SAGE). (Velculescu, V. E. et al. (1995), Serial Analysis of Gene Expression, Science 270: 484-487). Persons skilled in the art will appreciate that reagents for other amplification systems are added at appropriate steps in the process. For rolling circle amplification, for example, one may add one or more reporter sequences to the mixture in the second step, and perform enzymatic ligation in place of reverse transcription in the subsequent step.

Amplification assays may be end-point assays or real-time assays wherein the amplification mixture includes at least one reporter, for example, an intercalating dye such as SYBR green or dual-labeled fluorescent hybridization probes such as end-labeled linear probes for the 5' nuclease assay (U.S. Pat. No. 5,538,848), molecular beacon probes (U.S. Pat. No. 5,925,517), FRET probe pairs or yin-yang probes. Li, Q. et al. (2002), "A New Class of Homogeneous Nucleic Acids Probes Based on Specific Displacement Hybridization," Nucl. Acid. Res. 30: (2)e5). Probes may double as primers (Nazarenko, I. et al. (1997), A Closed Tube Format for Amplification and Detection of DNA Based on Energy Transfer, Nucl. Acids Res. 15: 2516-2521).

Amplification methods may also be used to generate quantities of double-stranded or single-stranded nucleic acid products for further processing, for example, sequencing, fragment analysis, or use in an assay such as the oligonucleotide ligation assay (OLA).

The Disruption Reagent may be prepared and supplied in dried form, for example a spot (which we call a "LysoDot") or a film (which we call a "LysoFilm") on the surface of a container or container portion to be used for preparing nucleic acids. A LysoDot or LysoFilm of Disruption Reagent may be applied to a tube, well, or cover, such as a lid, top or cap, of the container. The container may be a PCR tube, a microcentrifuge tube, a microtiter plate or a chip with wells, for example. The Disruption Reagent may be supplied in liquid form, preferably including a solvent such as DMSO, in a fine-barreled pipet suitable for dispensing small volumes, particularly nanoliter amounts. The Disruption Reagent may also be supplied as a dried pellet or as a composition dried onto a solid support, such as a fiber or a matrix or a bead that is inert and does not bind nucleic acids.

A chip or other microfluidic device may be constructed for carrying out the first and second steps of nucleic acid preparation in different chambers, and may include one or more additional chambers for subsequent processing.

Reagent kits may include dried Disruption Reagent, preferably LysoFilm- or LysoDot-containing containers or container portions, in combination with all or some reagents for performing at least one enzymatic process. Kits may include, for example, some or all RT reagents (primers, dNTPs, buffer, enzyme, RNase inhibitor, reducing agent). A DNase may be included. Similarly, some or all amplification reagents may be included (primers, dNTPs, buffer, polymerase), as may detection reagents (hybridization probes, which may be dual-labeled fluorescent hybridization probes, or intercalating fluorescent dye) or reagents for post-amplification processing, for example sequencing (enzyme, sequencing primer). Other enzymes may be included as appropriate.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Disruption Reagent according to this invention comprises a chaotropic agent, for example, a guanidium salt such as guanidine isothiocyanate or guanidine hydrochloride, or potassium iodide. Sodium hydroxide or potassium hydroxide may be substituted as an equivalent only for preparations of DNA alone, as that reagent destroys RNA. Our preferred chaotropic agent, guanidine isothiocyanate, tends to precipitate at low temperatures at concentrations of about 2 M and higher. Rather than heating the reagent and the dispensing apparatus, such as a pipet, a non-aqueous, water-miscible solvent that evaporates during processing, such as dimethylsulfoxide (DMSO) can be included in the Disruptive Reagent in minor amount, for example 1% (vol/vol) to keep the reagent liquid during dispensing. The Disruptive Reagent additionally contains a cell-lysing reagent, if the sample source may include intact cells. We utilize 0.25% sarcosyl detergent, although others may be used as well, as will be understood by persons skilled in the art. Additional ingredients may optionally be included in the Disruption Reagent. As indicated, our presently preferred Disruption Reagent includes 100 mM reducing agent, specifically βmercaptoethanol, and 0.01 M neutral buffer, specifically sodium citrate, pH=7.0.

As indicated, Disruption Reagent may be supplied for use either in liquid form or dry, as a LysoDot or LysoFilm as part of a container, in certain preferred embodiments. An example of an embodiment in which it may be preferred to dispense Disruption Reagent in liquid form is starting samples comprising cells in culture, such as cells grown in wells of microtiter plates. In that instance one may add liquid Disruption Reagent to the cells to form the reaction mixture. If the cells are relatively plentiful, say, numbering in the hundreds or thousands, one may reduce the mixture following disruption to a portion representing at least one, preferably fewer than 100, cells. Either some of the mixture can be removed, leaving the desired portion in the container for further processing, or the desired portion can be removed to a second container for further processing. The unused major portion can be stored or subjected to other processing. Reduction to a portion by either technique can be carried out after the second step of nucleic acid preparation as well.

Methods according to this invention are particularly adaptable to samples containing a small number of cells, for example a fraction of a cell up to 200 cells or 1-100 cells, or equivalent amounts of non-cellular sample materials. Methods according to this invention are particularly adaptable to processing that minimizes physical transfers of sample-containing mixtures, including performing nucleic acid preparation and nucleic acid amplification and detection in a single container. In order to design methods according to this invention it is convenient to calculate backwards. If a real-time assay is to be performed, for example, in a 100 μl-assay container (currently available thermal cycling instruments typically utilize 200 μl tubes that actually have a 100 μl-assay capacity), one takes into account the dilutions to be performed, either a single combined dilution or at least two and often three serial dilutions. In the serial-dilution method described above, the final dilution occurs with the addition of amplification and detection reagents, at least about a 9:1 dilution. The first dilution occurs in the second step of methods according to this invention and includes a dilution of at least 50:1. There may be at least one significant intermediate dilution such as reverse transcription with a dilution of up to 6:1, preferably not more than 2:1. Calculating backwards, one arrives at an appropriately small volume of Disruption Reagent for the first step of the method. The amount of Disruption Reagent is the amount of Disruption Reagent in liquid form before any drying to prepare, for example, a LysoDot. Applying the foregoing design principle to our work with 200 μl PCR tubes and 100 μl assays, we selected a volume of Disruption Reagent of 20-50 nl as an appropriate starting volume. Smaller volumes would, of course, be suitable as well. With guanidine isothiocyanate at a concentration of 2M, 20 nl of Disruption Reagent is sufficient for up to about 100 cells.

Freeing nucleic acids is performed at a chaotropic agent concentration of at least 2M. If the Disruption Reagent is added in liquid form, we prefer that the concentration of chaotropic agent be 2-8 M in the Disruption Reagent. If the Disruption Reagent is dried and rehydrated during use, it is reconstituted to the same concentration range. If evaporation is utilized as part of the first step of the reaction, the volume of Disruption Reagent added as a liquid or rehydrated from dried solid can be increased, and the concentration of chaotropic reagent decreased, prior to evaporation. The minimum 2 M concentration may be achieved through evaporation of water and volatile components, such as DMSO and β mercaptoethanol. More preferred embodiments start with Disruption Reagent containing at least 2 M chaotropic agent to minimize time of heating for evaporation.

In preferred methods, the first step includes incubation with heat to reduce the mixture of sample and Disruption Reagent to a wet or semi-dry solid or even a dry solid, taking care not to lose nucleic acids or at least keep the loss below 25%. Such heating is preferred for three reasons. First, it concentrates the chaotropic agent to a very high concentration, ensuring release of nucleic acids. Second, it reduces the incubation time needed and provides visual assurance that release has been achieved. Third, it removes volatile agents that might deleteriously affect subsequent processing. For our laboratory preparations, we typically open the tube at the end of the heating step and place the lid holding the lysed sample under a microscope for inspection. That procedure would not be preferred for applications in which avoiding contamination is particularly important, such as in processing human samples.

The second step in methods according to this invention is a major dilution step. In certain preferred embodiments this occurs in the same container. In embodiments in which the container includes flow channels, such as a chip, mixture from a first chamber, such as a well, in which the first step is performed, may flow into a separate chamber for dilution. In all cases, the second step is performed without first separating nucleic acids from degraded proteins. Except in certain embodiments in which one wishes to eliminate either RNA or DNA, the second step is performed without separating DNA molecules from RNA molecules. The degree of dilution is at least 50:1 of the amount of Disruption Reagent containing 2 M chaotropic reagent. Thus, if the first step was performed with a volume of liquid Disruptive Reagent with 2 M chaotropic agent, dilution is at least 50:1 on a volume-to-volume basis. If the first step was performed starting with a larger volume of Liquid Disruption reagent with 1 M chaotropic agent that was concentrated during the first step, dilution is at least 25:1 on a volume-to-volume basis, and so forth. Following dilution, the sample is prepared. The mixture is ready for further processing of nucleic acids, RNA or DNA or both, without removal of degraded proteins and without removal of Disruptive Reagent. Illustrations of use are set forth in the Examples.

Figure 4:
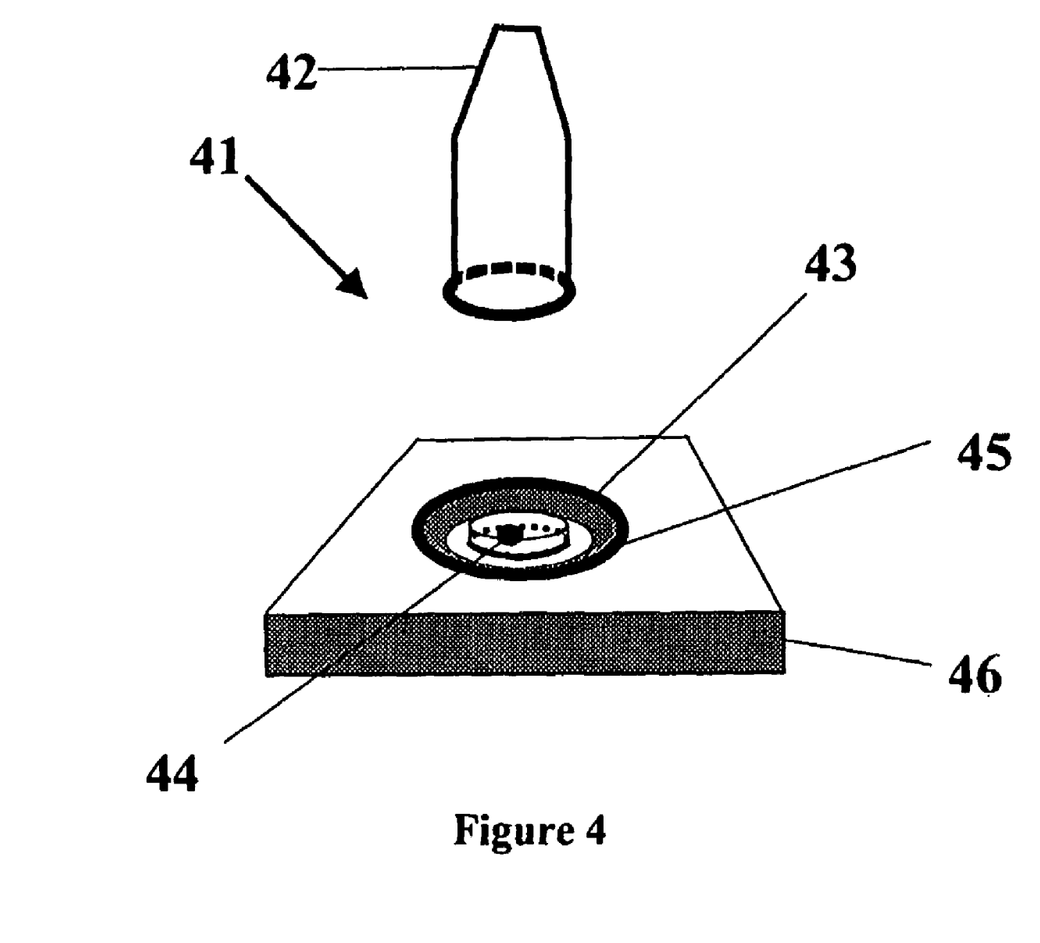
FIG. 4 is a perspective view of a container including a LysoDot.

Disruption Reagent may be supplied in dried form as part of a container, as discussed above. An embodiment is depicted in FIG. 4. For our own laboratory preparations, including Example 1 below, we have simply dried the LysoDots in air, which is much slower than using a heating block as depicted in FIG. 4, and the lysed samples on a rack placed in a water bath maintained at about 75° C. FIG. 4 shows a container 41, a PCR tube, more specifically a 200 µl PCR tube. Container 41 comprises body 42 and sealing cap 43. Dried Disruption Reagent, in the embodiment LysoDot 44, is adhered to cap 43. Preparation of the container part 43 with adhered LysoDot 44 was as follows: a small amount, in our case, 20 nl of Disruption Reagent was added to cap 43 resting in depression 45 of heat block 46. The Disruption Reagent was heated until it dried to LysoDot 44, adhering to cap 43. LysoDot 44 could equally be placed in body 42 and dried there. We chose to put it into cap 43 only because of the ease of pipetting Disruption Reagent by hand onto the center of cap 43. We have carried out the first step of methods according to this invention in cap 43, by adding thereto a sample, for example, embryonic cells in isotonic solution, namely phosphate-buffered saline (PBS), thereby rehydrating the dried Disruption Reagent. Tube 41 may then be closed for incubating and evaporating the mixture to a semi-dry or dry solid. At this point the mixture can be used immediately or it can be frozen or refrigerated. Heating/evaporation is carried out under conditions avoiding cross-contamination of samples. Closing tube 41 is one way to avoid that occurrence. Other ways will be apparent to persons skilled in the art.

Next, the fifty-fold dilution solution is added to cap 43, having opened tube 41 if necessary. At this point it is desirable to utilize tube 41 right-side up, so we reseal the tube and cause the mixture to move to tube body 42. Centrifugation may be used to facilitate the transfer. Subsequent processing is carried out in the tube in its upright position.

Figure 5:
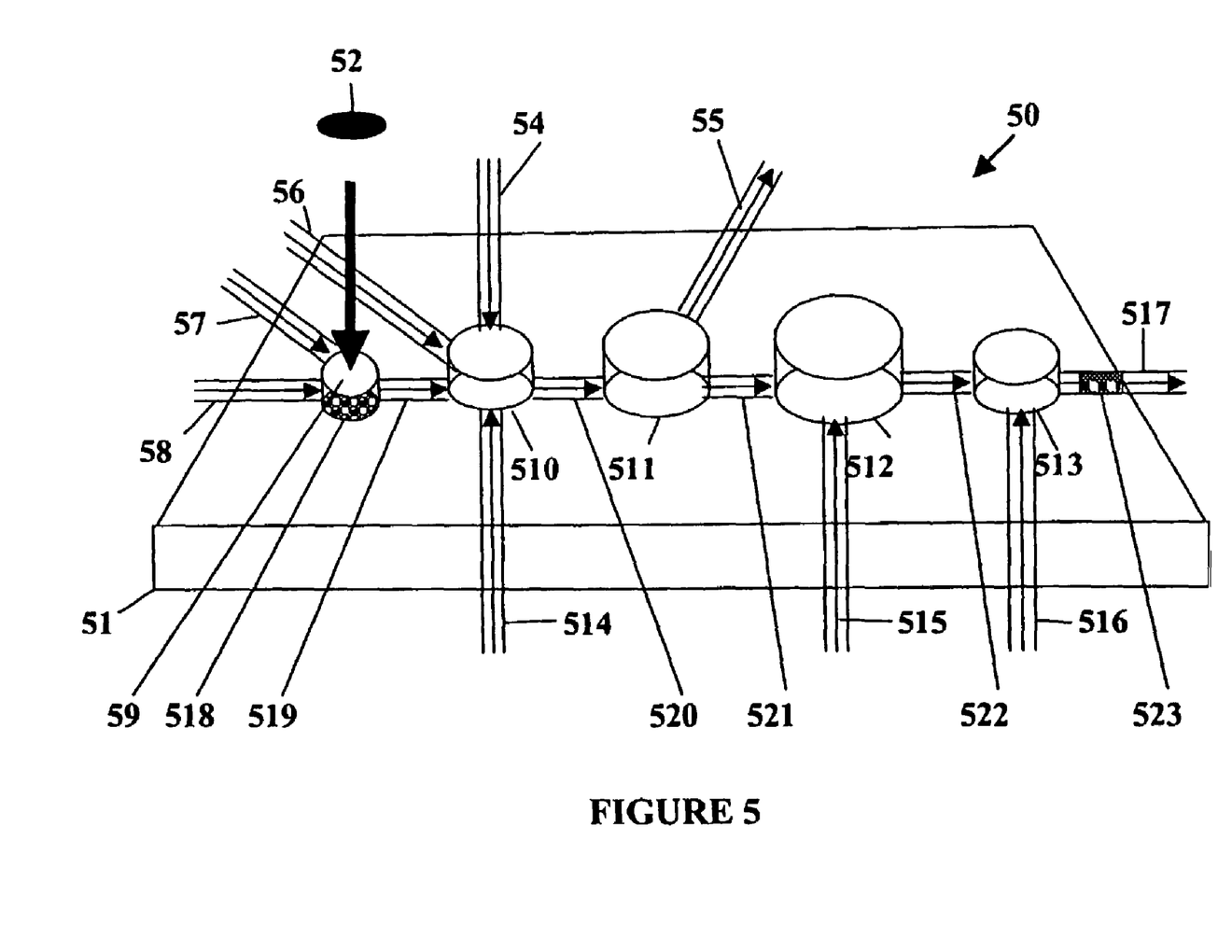
FIG. 5 is a cross-sectional view of a chip containing a first chamber for performing the first step of preparation according to this invention and a second chamber for performing the second step according to this invention.

Another LysoDot- or LysoFilm-containing apparatus is shown in FIG. 5. FIG. 5 depicts an apparatus 50 through which reagents are moved under control during processing. Apparatus 50 may be, for example a chip having wells and chambers. Chip 50 includes a well 59 containing dried Disruption Reagent, in this case LysoFilm 518. A sample may be added to well 59, which can then be closed with cap 52. The sample, now containing liquefied Disruption Reagent, could be moved to chamber 510 through channel 519, controlled by means not shown, by pressure applied through port 57 or 58, for incubation, drying and dilution in the second step. Chamber 510 is connectable to a source of dilution reagent by means of channels 54, 56, 514. Alternatively, incubation and heating (drying) could be carried out in well 59, after which the mixture could be liquefied and delivered to chamber 510 by means of all or some of the dilution reagent. The prepared mixture could then be delivered, by controllable means not shown, or by pressure applied through port 57 or 58 to one or more chambers 511, 512, or 513, etc for further processing. Chambers 511, 512, 513 are connectable to reagent supply sources by additional channels, for instance 515, 516. A fraction of the material in chamber 511 can be removed by channel 55. Positive gas pressure in the system can be released through channel 517 that contains a filter 523 to prevent the escape of non-gaseous molecules. In one design, the block, 51, in which these channels and wells are built is comprised of a material that can rapidly heated and cooled, and in the most preferred case can be heated and cooled be differently for different wells and chambers. In another design, the block 51 is comprised of insulating material that is not easily heated or cooled, and temperature changes are achieved through at least one surface of each chamber, by means not shown. In yet another design, the entire block 51 is cooled continuously and the temperature is raised by means not shown, for example by resistance heating, through the surface of each chamber or by passing infrared light into each chamber. In preferred designs at least one surface of each chamber is transparent to permit transmission of light into the chamber. In preferred designs all surfaces within the chamber are made from or coated with inert materials which do not bind nucleic acids or other chemicals or proteins. In preferred designs the chambers and channels are designed to minimize turbulence or drag of flowing liquids. Numerous variations of LysoDot preparations are included in this invention. In addition to removable caps or lids, LysoDots can be adhered to any surface suitable for use in carrying out the first method step, for example, attached lids or bodies of PCR tubes, microscopy slides or cover slips, wells of multiwell trays. The Disruption Reagent may also be supplied as dried pellet or as a composition dried onto a solid support, such as a fiber or matrix, or bead, that is inert and does not bind nucleic acids. For purposes of this application such a solid support is considered a container or container part for appropriate use.

Numerous variations are possible following the first step in methods according to this invention. The incubation of the first step may include heating to dry the mixture, after which it can be stored frozen at, for example, −20° C., for long periods or even stored at room temperature for significant periods. Further, use of the mixture resulting from the first incubation step of preparation may proceed by a series of separate steps, as outlined above, or two or more steps may be combined. For example, reverse transcription and amplification reagents may be included in a single reagent that dilutes by at least about a factor of nine. The second step, at least fifty-fold dilution, can be combined with subsequent steps in appropriate cases. It will be appreciated that thermostable enzymes are required for processing at high temperatures needed, for example, for strand melting.

If it is desired to utilize RNA only, DNA can be degraded by a DNA endonuclease, for example, DNase I. Degradation may follow the second step of purification, or DNA endonuclease may be included in the dilution reagent used in the second step, together with salts required for the activity of the DNA endonuclease that is used. Following elimination of DNA, a chelating agent is added at a concentration sufficient to prevent magnesium-dependent hydrolysis of RNA, and the mixture is heated, for example for 10 minutes at 65° C., to inactivate the endonuclease prior to reverse transcribing RNA to cDNA.

Particularly for applications such as microarray analysis, we have utilized a DNase digestion step preceding reverse transcription in our single-tube format for Xist/Sry analysis reported below in Example 1. We analyzed the efficiency with which genomic DNA in morula-stage mouse embryos was degraded. In the fifteen male samples analyzed, we determined that 96 percent of the DNA had been degraded. In the ten female samples analyzed, RNA recovery was lower than in non-treated samples. Some loss of RNA by a DNase step was expected. Our RNA recovery, however, was considerably higher than we obtained with traditional RNA extraction using either a Micro RNA Isolation Kit (Stratagene, La Jolla, Calif., U.S.A) or an RNeasy Mini Kit (Qiagen, Inc., Valencia, Calif., U.S.A.) coupled to DNase digestion. Other enzyme treatments may be included in or following the second step as may be appropriate. For example, one may digest plant cell walls or other components using a glycosidase enzyme, or one may digest bacterial cell walls using lysozyme.

Another processing variation is to avoid reverse transcription for all or a portion of a prepared mixture. For example, a mixture resulting from the second step may be divided into two portions. One portion may be further processed by RT-PCR to quantify total cDNA plus genomic DNA. The other portion may be further processed without reverse transcription such that only genomic DNA is amplified. Reverse transcription can be avoided in any suitable manner, including by omitting reverse transcriptase, by omitting primers for reverse transcription, or by destroying RNAs with an RNase.

Division of mixture following the second step or later in processing may be done for other reasons. For example, rather than performing a multiplex assay with multiple primer pairs and multiple hybridization probes, a mixture may be divided for parallel non-multiplex assays.

Other processing variations may also be used. For example, RNAs may be prepared according to this invention, labeled directly or as reverse-transcribed cDNA, and subjected to hybridization and analysis on a microarray of immobilized oligonucleotides.

EXAMPLES

Example 1

Assays

Sample preparation was performed according to this invention, followed by real-time multiplex PCR assays, all in a single tube. Processing subsequent to preparation, that is, following the second step, utilized the assay materials and methods reported in Hartshorn, C. et al (2002), Developmentally-Regulated changes of Xist RNA Levels in Single Pre-implantation Mouse Embryos, as Revealed by Quantitative Real-Time PCR, Mol. Reprod. Dev. 61: 425436; and Hartshorn, C. et al (2003), Differential Patterns of Xist RNA Accumulation in Single Blastomeres Isolated from 8-Cell Stage Mouse Embryos Following Laser Zona Drilling, Mol. Reprod. Dev. 64: 41-51, both of which are incorporated herein in their entirety. Six mouse embryos were grown to the blastocyst stage, as detailed in the first paper cited above. All experimental procedures were carried out rigorously following precautions aimed at avoiding or destroying environmental RNase contamination as described in both papers cited above. LysoDots were prepared several days before embryo collection by delivering 20-nl aliquots of Disruption Reagent to the lids of reaction tubes. Precise measurement of droplet size was obtained following the method previously described by Wangh (Wangh, L. J. (1989), Injection of $Xenopus$ Eggs Before Activation, Achieved by Control of Extracellular Factors, Improves Plasmid DNA Replication after Activation, J. Cell Sci. 93:1-8). The Disruption Reagent composition was:

0.25% Sarcosyl

2 M Guanidine Isothiocyanate 100 mM β Mercapto-ethanol

1% (vol/vol) Dimethylsulfoxide 0.01 M Sodium Citrate, =pH 7.0

LysoDots of 20 nl were allowed to dry by placing open tubes under a hood, in sterile conditions. Most droplets dried overnight, but some required 48 hours for crystallization to occur. No difference was observed among these samples in terms of experimental results. Tubes were closed and stored upside down at room temperature until use.

Immediately before harvesting, individual embryos were placed in 3 ml of Dulbecco's PBS. Each embryo was then aspirated into a glass capillary having an internal diameter of 0.2 mm and tapered at the end so that the inner volume of the tapered tip would contain about 20 nl. Tapering was obtained by pulling the glass capillaries in a Micro-Pipette Puller (Industrial Science Associates, Inc., Ridgewood, N.Y.). A blunt conical end was then produced by gently removing the thinnest portion of the tip with an abrasive stone. For an optimal delivery of the embryo to the LysoDot, PBS was aspirated into the pipette slightly beyond the tapered end. The embryo was allowed to move toward the pipette's tip and was then expelled directly onto the dry LysoDot in a volume of PBS that was as close as possible to 20 nl (some PBS was left in the pipette). This whole procedure was carried out under a microscope, so that the embryo's position in the pipette could be monitored. Microscopic observation also made it possible to check for an immediate and complete dissolution of the LysoDot crystals upon addition of the embryo-containing PBS.

Tubes were closed upside down and transferred in this position to a rack placed in a closed bath heated to 75-77° C. Incubation was carried out for 5 minutes. After this step, the sample-containing mixtures were mostly dry or partially dry, due to evaporation. They were stored upside down at −20° C. until the next step.

The second step of preparation was next carried out. In this case, because the example includes reverse transcription, the dilution reagent contained oligonucleotides in addition to water. The tubes were opened again under a microscope and each dry droplet was re-solubilized by addition of 61 µl of a mixture of Random Hexamers (4.2 ng/µl) in DEPC-treated water (all reagents were from a ThermoScript™ RT-PCR System kit, Invitrogen, Life Technologies, Carlsbad, Calif., USA). Tubes were closed and briefly placed, still in the upside down position, on a vortex. Samples were then centrifuged, mixed again on the vortex (right-side up) and spun down one more time.

The closed tubes containing the prepared nucleic acid samples were heated to 65° C. for 5 min to melt double-stranded RNA molecules and then cooled to hybridize the oligonucleotide primers to sequences within the RNA molecules. Then the tubes were opened for addition of 4 µl of reverse transcriptase solution, which diluted the mixture by a factor of about 1.7 volume increase. The solution contained 0.5 µl of ThermoScript reverse transcriptase (15 U/µl), 1 µl of 10 mM dNTP Mix, 0.5 µl of RNaseOUT™ (40 U/µl) and 2 µl of 5× cDNA Synthesis Buffer (250 mM Tris acetate, pH 8.4, 375 mM potassium acetate, 40 mM magnesium acetate). The tubes were closed and incubated for 10 min at 25° C. followed by 50 min at 55° C. to prepare cDNA copies of RNA. The reaction was terminated by heating the closed tubes for 5 min at 85° C., which denatured the reverse transcriptase. Next, the tubes were cooled on ice, centrifuged briefly and opened for addition of 0.5 µl of *E. coli* RNase H (2 U/µl). Incubation was carried out for 20 min at 37° C. in order to degrade the RNA molecules present in the sample. Samples were cooled and centrifuged again, and stored at 20° C. until the next step.

In one experiment, the full volume of each sample was transferred to a PCR tube where it was mixed with 89.5 µl of complete PCR amplification and detection reagents. The reagents comprised 54.3 µl of PCR-grade water, 10 µl of 1 M Tris chloride, pH 8.3, 16 µl of 25 mM magnesium chloride, 4 µl of 10 mM dNTP (2'-deoxynucleoside 5'-triphosphates) Mix, 3 µl of a 10 µM mix containing the upper and lower primers for amplification of a sequence of DNA and RNA from the gene Xist and the upper and lower primers for amplification of a sequence of the gene Sry, molecular beacon probes for the amplicon of the Xist gene and for the amplicon of the Sry gene (0.3 µl each of 100 µM solutions), and 1.6 µl of a mix containing 4 U of Taq polymerase (Promega, Madison, Wis.) complexed to Platinum Taq antibody (Invitrogen, Carlsbad, Calif.) by means of a 5 min incubation at room temperature prior to addition to the PCR solution. Amplification and detection were carried out in an ABI Prism 7700 Sequence Detector. The cycling profile was: 95° C. for 5 min; 10 cycles consisting of the following three steps: 95° C. (20 sec), 57° C. (60 sec), 72° C. (30 sec); 45 cycles with the following three steps: 95° C. (20 sec), 53° C. (60 sec), 72° C. (30 sec).

Figure 1:
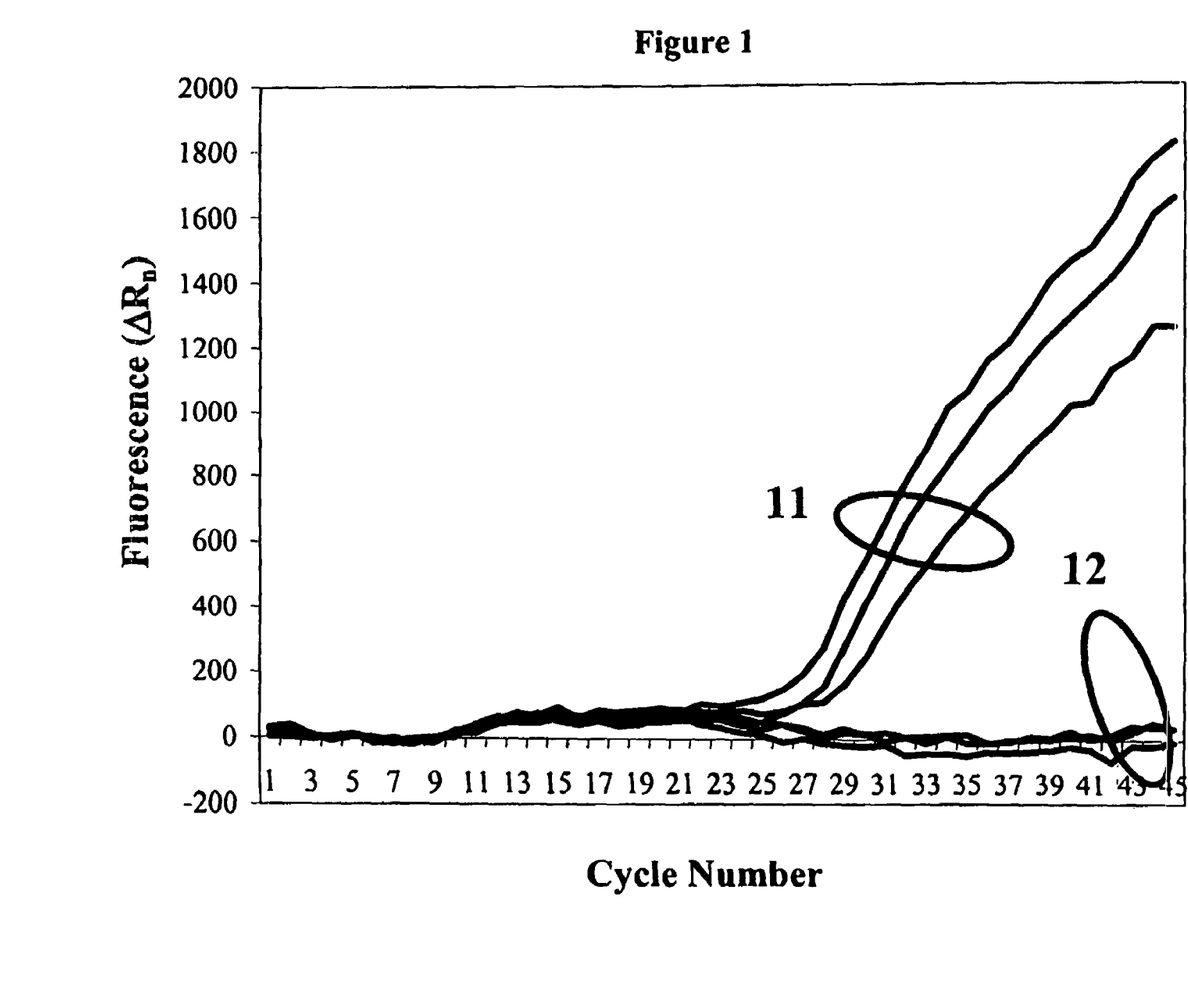
FIG. 1 is a graph of results of PCR assays for a first target sequence performed on replicate nucleic acid samples prepared according to this invention.
Figure 2:
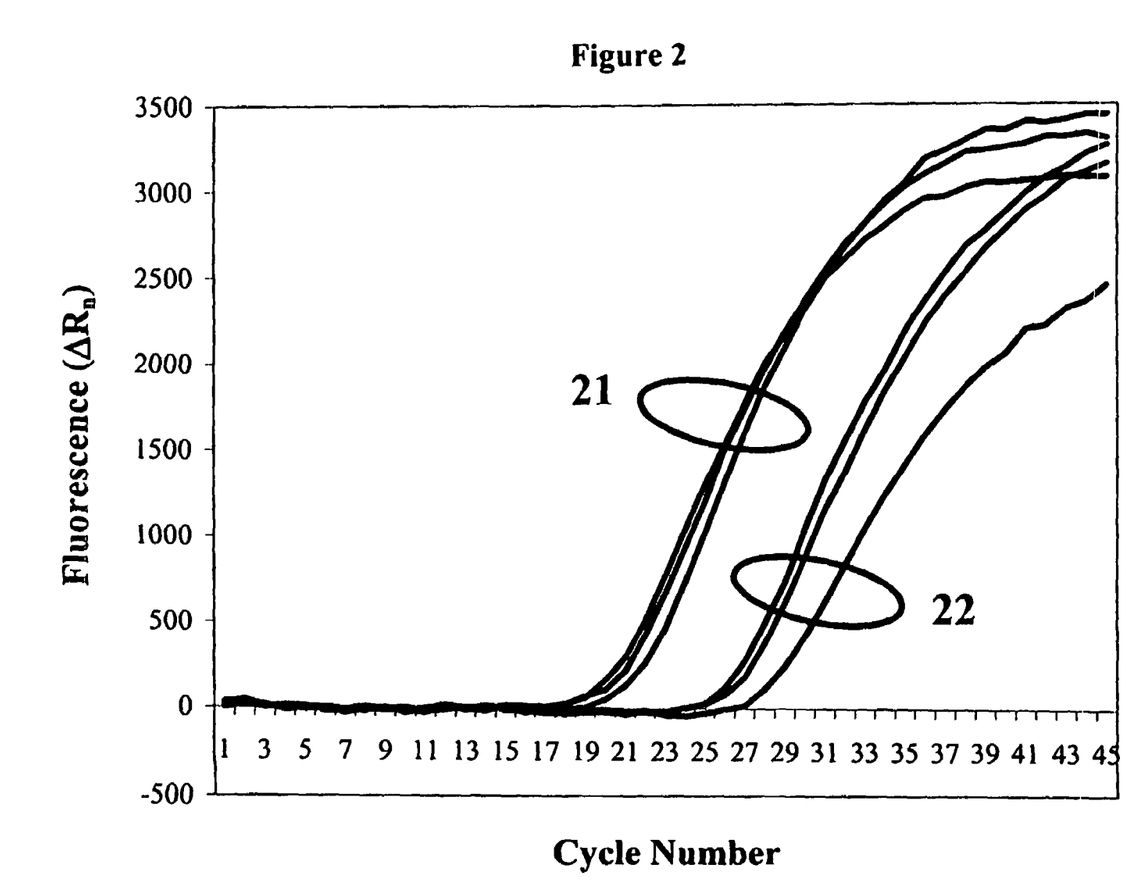
FIG. 2 is a graph of results of PCR assays for a second target sequence performed on replicate nucleic acid samples prepared according to this invention.

Assay results are shown in FIGS. 1 and 2. Referring to FIG. 1, it can be seen that three embryos (Circle 11) had an Sry signal and, therefore, were male, while the other three embryos (Circle 12) had no Sry signal and, therefore, were female.

It is known that female blastocysts express high levels of Xist RNA, responsible for inactivation of one X chromosome, while male embryos have virtually no Xist. The results obtained with preparation according to this invention fully confirmed this expectation. Referring to FIG. 2, it can be seen that all three female embryos (Circle 21) generated signals detectable above background approximately six thermal cycles sooner than the male embryos (Circle 22).

As indicated above, no processing of samples was performed between reverse transcription and PCR. The results demonstrate the effectiveness of this invention to directly prepare samples for amplification and further demonstrate that all processing could be performed in a single tube. In other experiments all steps were performed successfully in a single PCR tube to the cap of which we had initially added a LysoDot. For example, we have used the single-tube assay on the following samples: two-, three- four- and eight-cell mouse embryos and mouse embryos at the blastocyst stage, single blastomeres isolated from four and eight-cell mouse embryos, and mouse embryos treated with DNase (see Example 3 below).

Example 2

Quantitation

Figure 3:
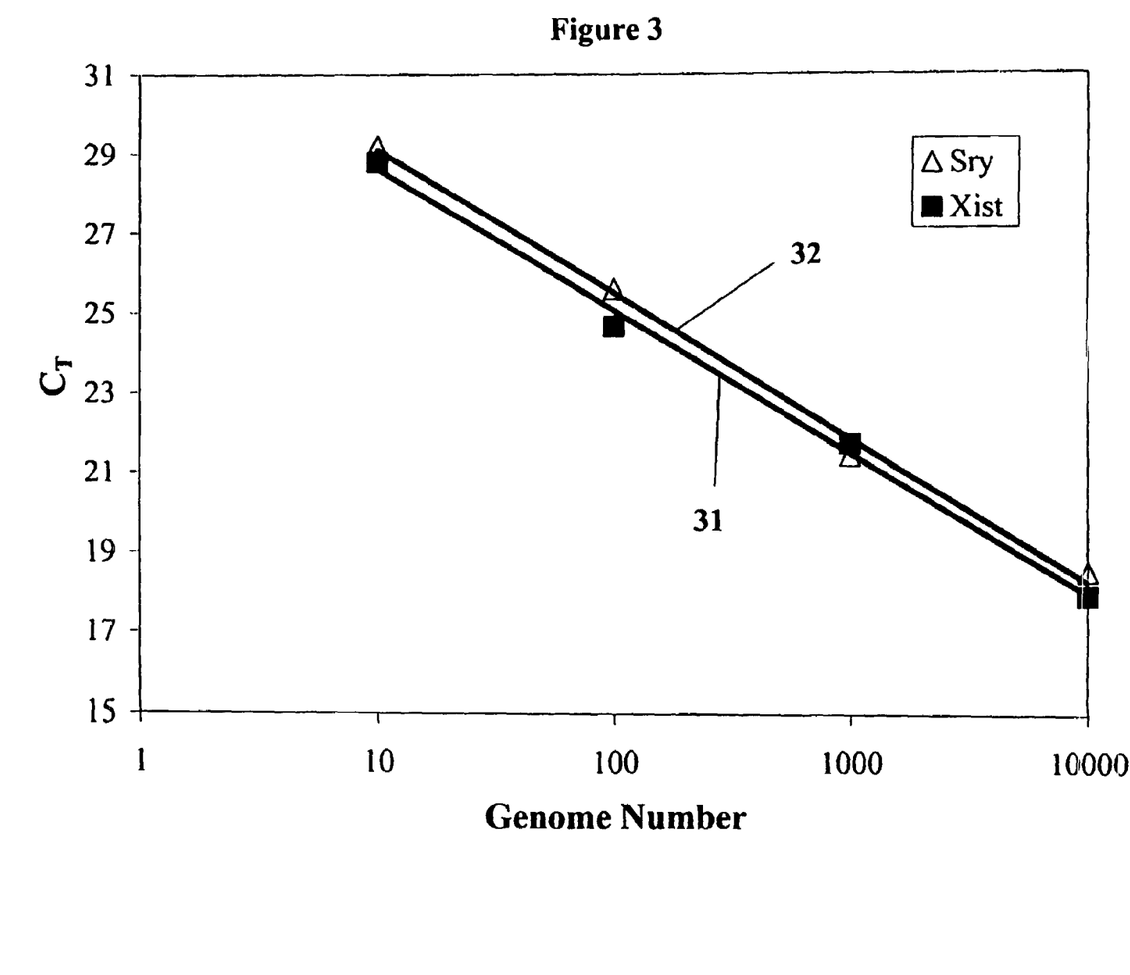
FIG. 3 is a plot of PCR assay results sequence and the second target sequence with standard amounts of nucleic acid samples.

Control reactions containing decreasing amounts of male mouse genomic DNA (10,000 genomes down to 10 genomes) were used to construct linear plots of Genome Number vs. $C_T$, the thermal cycle at which signal becomes detectable above background. Results are shown in FIG. 3. The plots for both the Xist (Curve 31) and Sry (Curve 32) signals fall on straight lines that virtually overlap. Comparison of the $C_T$ values of the curves of Circle 21 in FIG. 2, which have a $C_T$ of about 19, with standard curve 31 of FIG. 3 and the curves of Circle 22, which have a $C_T$ of about 25, with standard curve 31 of FIG. 3, allow us to calculate that each embryo contains about 100 genomes and each female embryo contains several thousand copies of Xist RNA (cDNA). These results are very similar to our previous findings, reported in the above-identified papers, based on a traditional approach to nucleic acids extraction from mouse embryos.

None of the male embryos assayed with the sample preparation method of this invention as part of a single-tube assay had levels of Xist DNA greater than the levels of Sry DNA. This is seen by comparing the $C_T$ values of the curves in Circle 11 (FIG. 1) with the $C_T$ values of the curves in Circle 22 (FIG. 2). This result is consistent with the absence of Xist gene expression in male embryos and the presence of one X chromosome (one Xist gene) and one Y chromosome (one Sry gene) in each male cell. Two of the male embryos have about 100 genomes, as expected, while the third male embryo was probably composed of fewer cells (a finding not unusual for cultured embryos). In the female embryos the presence of Xist RNA in addition to Xist genomic DNA leads to the detection of thousands of Xist template copies in each sample.

Example 3

DNase Treatment

The efficiency of DNase treatment in samples prepared with the method of this invention was tested as follows.

Thirty-five mouse embryos at the morula stage (about 16-32 cells) were collected individually on LysoDots and disrupted as detailed for Example 1, the difference being that embryos were purchased frozen at the 8-cell rather than the 2-cell stage. Each assay was carried out from beginning to end in the same 200 µl PCR-grade tube (microAmp Optical Tubes, Applied Biosystems, Foster City, Calif.), although the lids (Optical Caps, AppliedBiosystems) were replaced every time the tubes were opened in order to avoid contamination. Ten samples were processed completely as in Example 1, thus containing both genomic DNA and cDNA at the end of the assay, and were designated as controls. In the remaining 25 samples the second step of preparation was modified to allow genomic DNA degradation, as explained below, so that in this protocol reverse transcription became the third step of preparation and PCR the fourth. Particular care was taken in assigning embryos with equivalent developmental and morphological features to the Control and the DNase-Treated groups.

Each disrupted and heated sample (dry or partially dried) was resuspended on the lid originally containing the LysoDot with 4 µl of DNase Mix having the following composition:
DNase Mix (reagents ration for 10 µl):
  1 µl 10× Reaction Buffer (Invitrogen, Life Technologies, Carlsbad, Calif.) containing 200 mM Tris-HCl, pH 8.4, 20 mM $MgCl_2$, and 500 mM KCl
  0.5 µl DNase I (2 U/µl) (Ambion, Inc., Austin, Tex.)
  8.5 µl Nuclease-free $H_2O$ (Ambion)
A 200-fold dilution of the reagents originally comprising the LysoDot was thus achieved in this step, bringing the concentration of guanidine in the DNase digestion step to 10 mM (2 M diluted 200:1), at which concentration the enzymatic reaction was not inhibited.

Tubes were closed, vortexed in the upside-down position, inverted and centrifuged as described in Example 1. Digestion of the genomic DNA in the samples was carried out for 20 minutes at room temperature, after which the reaction was terminated by adding 1 µl/assay of a 10 mM EDTA solution (molecular biology grade, Invitrogen) and heating at 65° C. for 10 minutes. As known to those skilled in the art, the addition of a chelating agent is needed in order to avoid magnesium-dependent RNA strand scission during the heating step which denatures the DNase, therefore blocking its further activity when cDNA is produced during the reverse transcription of RNA.

After DNase treatment, each sample received 2 µl or Random Hexamer Primer Mix prepared as follows:
  0.5 µl Random Hexamers (50 ng/µl)
  0.5 µl DEPC-treated $H_2O$
(Both reagents from Invitrogen, as described in Example 1.)
The total volume of each assay at this point was 6 µl. After incubation of the primers with RNA, as detailed in Example 1, reverse transcription reagents were added in a volume of 4 µl and all the remaining steps of reverse transcription and PCR were also carried out as described in Example 1.

The results indicated that, in the average, 42.6 copies per embryo of genomic Xist plus Sry DNA were recovered from male control samples, corresponding to an average number of 21.3 cells per embryo and confirming the expected cell number for embryos at the morula stage based on the fact that one male cell contains one copy of each of these two genes. After DNase treatment, only 1.6 copies per embryo of genomic Xist plus Sry DNA were left in the male samples, or 4% of the control value, indicating that DNase activity in the presence of 10 mM guanidine and under the experimental conditions utilized was optimal and degraded 96% of the DNA present. (In a parallel experiment, DNase incubation carried out for 15 rather than 20 minutes resulted in the degradation of 90% of genomic DNA in male samples.) This level of effectiveness was judged to be very high, because it is known that DNase I cleaves DNA at low concentration rather inefficiently, having poor affinity for its substrate.

Not unexpectedly, RNA recovery was partially affected by the presence of the DNase step. As widely debated in the literature, there is no ideal method allowing complete DNA digestion without altering RNA recovery.

In this assay, the average Xist RNA recovery from DNase-treated female samples was lower than the Xist RNA recovery from female controls. The amplification of DNA templates during PCR was unaffected by the presence of the DNase Mix reagents.

A number of embodiments of the invention have been described. Nevertheless, it will be understood that various modifications may be made without departing from the spirit and scope of the invention.

What is claimed is:

1. A single-container method for synthesizing cDNA from RNA in a biological sample using a reverse transcriptase and amplifying and detecting at least one selected sequence of said cDNA, comprising:
   a) combining said biological sample with a disruption reagent comprising a chaotropic salt having a concentration of at least 2M that denatures or degrades all proteins to produce a disrupted sample containing RNA freed from bound proteins and inactivating nucleases with no more than twenty-five percent loss of RNA;
   b) reducing the concentration of said chaotropic salt in said disrupted sample to less than 0.05M by diluting without washing the disrupted sample with at least one aqueous reagent before adding the reverse transcriptase;
   c) incubating the diluted, disrupted sample with reverse transcriptase to transcribe said RNA to cDNA;
   d) amplifying at least one selected sequence of said cDNA; and
   e) detecting the at least one amplified cDNA sequence
   wherein steps b) through e) are performed without first separating the RNA from degraded proteins or from said chaotropic salt.

2. The method according to claim 1, wherein said disruption reagent comprises a cell-lysing detergent.

3. The method according to claim 2, wherein said biological sample comprises at least one cell.

4. The method of claim 1, wherein step a) comprises heating to concentrate the chaotropic salt after combination of the biological sample with the disruption reagent.

5. The method of claim 4, wherein the initial concentration of said chaotropic salt is at least 2M.

6. The method of claim 4, wherein said heating is sufficient to produce a disrupted sample that is at least semi-dry.

7. The method of claim 6, wherein said disruption reagent comprises a water-miscible solvent that prevents precipitation of the chaotropic salt and that evaporates during said heating.

8. The method of claim 1, wherein the chaotropic salt is a dry reagent that is dissolved in the biological sample.

9. The method of claim 1, wherein the container is a microfluidic device.

10. The method of claim 1, wherein in step b) the concentration of chaotropic salt is reduced to less than 0.01M.

11. The method of claim 10, wherein the chaotropic salt is a dry reagent that is dissolved in the biological sample.

12. The method of claim 11, wherein the biological sample comprises phosphate buffered saline (PBS).

13. The method of claim 11, wherein said dry reagent is adhered to a surface of the container.

14. The method of claim 13, wherein said surface is the inner surface of a tube, a tube cap, a wall of a microtiter plate, or a microtiter plate cover.

15. The method of claim 11, wherein the chaotropic salt has a concentration of at least 2M when dissolved in the biological sample.

16. The method of claim 15, wherein step a) comprises heating to concentrate the chaotropic salt after combination of the biological sample with the disruption reagent.

17. The method of claim 4 wherein step b) comprises diluting with water comprising random hexamers, heating to denature double strands, and cooling to anneal the random hexamers to the RNA.

18. The method of claim 17, wherein step c) comprises adding reverse transcriptase and RT buffer in an amount that does not further dilute the disrupted, diluted sample from step b) by more than a factor of six.

19. The method of claim 18, wherein in step d) amplification is carried out in amplification buffer added in this step and wherein that addition dilutes the cDNA by a factor of at least nine.

20. The method of claim 16, wherein the initial concentration of chaotropic salt is at least 2M.

21. The method of claim 20, wherein said heating is sufficient to produce a disrupted sample that is at least semi-dry.

22. The method of claim 21, wherein said disruption reagent comprises a water-miscible solvent that prevents precipitation of the chaotropic salt and that evaporates during said heating.

23. The method of claim 22, wherein the solvent is DMSO.

24. The method of claim 22, wherein said disruption reagent comprises a cell-lysing detergent.

25. The method of claim 24, wherein said biological sample comprises at least one cell.

26. The method of claim 21, wherein step b) includes diluting progressively with three aqueous solutions a first solution comprising DNase, a second solution comprising a chelating agent, and a third solution comprising random hexamers, and wherein the container is heated following addition of the chelating agent.

27. The method of claim 1 wherein amplification and detection reagents are added in step c) and wherein step c) further dilutes the disrupted, diluted sample by at least a factor of nine.

28. The method of claim 1, wherein the proteins that are denatured or degraded comprise nucleases.

\* \* \* \* \*